United States Patent
Lang et al.

[11] Patent Number: 5,254,135
[45] Date of Patent: Oct. 19, 1993

[54] METHODS FOR DYEING KERATINOUS FIBRES WITH AMINOINDOLES, COMPOSITIONS AND DEVICES FOR USE

[75] Inventors: Gerard Lang, Saint-Gratien; Alex Junino, Livry-Gargan; Jean Cotteret, Verneuil-sur-Seine, all of France

[73] Assignee: L'Oreal, Paris, France

[21] Appl. No.: 915,649

[22] Filed: Jul. 21, 1992

Related U.S. Application Data

[63] Continuation of Ser. No. 599,800, Oct. 22, 1990, abandoned.

[30] Foreign Application Priority Data

Oct. 20, 1989 [FR] France ............................. 89 13788
Mar. 16, 1990 [FR] France ............................. 90 03436

[51] Int. Cl.$^5$ ............................................. A61K 7/13
[52] U.S. Cl. .................................. 8/408; 8/406; 8/409; 8/423; 8/428; 424/70; 564/440; 564/441
[58] Field of Search ............... 8/406, 407, 408, 409, 8/414, 416, 423, 428; 424/70; 564/440, 441

[56] References Cited

U.S. PATENT DOCUMENTS

| | | | |
|---|---|---|---|
| 4,013,404 | 3/1977 | Parent et al. | 8/423 |
| 4,425,132 | 1/1984 | Grollier et al. | 8/408 |
| 4,932,977 | 6/1990 | Schultz | 8/406 |

FOREIGN PATENT DOCUMENTS

| | | |
|---|---|---|
| 0271186 | 6/1988 | European Pat. Off. |
| 0348280 | 12/1989 | European Pat. Off. |
| 2716671 | 10/1978 | Fed. Rep. of Germany |
| 262173 | 7/1989 | France |
| 2213169 | 3/1988 | United Kingdom |

OTHER PUBLICATIONS

French Search Report of FR 89 13788.
S. T. N. Serveur De Bases Donnees, Karlsruhe, DE; Fichier Registry, RN=53918-91-5 & Fichier Chemical Abstracts, vol. 81, No. 151898.

Primary Examiner—Paul Lieberman
Assistant Examiner—William S. Parks
Attorney, Agent, or Firm—Cushman, Darby & Cushman

[57] ABSTRACT

Method for dyeing keratinous fibres, in particular human keratinous fibres, such as hair, characterized in that a composition (A) containing, in a medium appropriate for dyeing, at least one aminoindole corresponding to the formula:

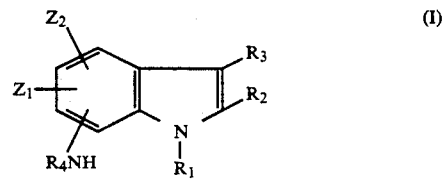

in which:
$R_1$ and $R_3$, independently of one another, represent a hydrogen atom or a $C_1-C_4$ alkyl group;
$R_2$ denotes hydrogen or a $C_1-C_4$ alkyl group or COOR', R' being a hydrogen atom or a $C_1-C_4$ alkyl group;
$R_4$ represents a hydrogen atom or a $C_1-C_4$ alkyl, $C_1-C_4$ hydroxyalkyl or $C_2-C_4$ polyhydroxyalkyl group;
$Z_1$ represents a hydrogen or halogen atom or a $C_1-C_4$ alkyl group or OR;
R being a hydrogen atom or a $C_1-C_4$ alkyl group; and
$Z_2$ represents a hydrogen atom or a $C_1-C_4$ alkyl group;
and its salts
is applied to said fibres, the colour being developed with the aid of an oxidizing system.

34 Claims, No Drawings

METHODS FOR DYEING KERATINOUS FIBRES WITH AMINOINDOLES, COMPOSITIONS AND DEVICES FOR USE

This is a continuation of application Ser. No. 07/599,800, filed Oct. 22, 1990 now abandoned.

The present invention relates to new methods for dyeing keratinous fibres and in particular human keratinous fibres, such as hair, using an aminoindole, and to tinctorial compositions and to devices enabling these methods to be used.

The dyes of the indole family and in particular 5,6-dihydroxyindole and its derivatives are well known for their use in dyeing keratinous fibres and in particular human hair.

French Patents FR-A-1 133 594, 1 166 172 and 2 390 158 propose methods for dyeing with the aid of 5,6-dihydroxyindole, using metal cations playing the role of melanogenesis promoter.

5,6-Dihydroxyindole leads in particular to black or more or less grey hues.

Various dyeing methods using indole derivatives in combination with oxidizing systems, such as inorganic anions, such as, for example, iodide, or metal anions, such as permanganate or bichromate, have also been described in FR-A-2 593 061, 2 593 062 and 2 594 331.

The inventors have just discovered that a particular category of indoles substituted on the aromatic ring by an amine function enabled particularly valuable and powerful hues to be obtained when the dyeing is developed by oxidizing agents.

The invention therefore relates to a method for dyeing keratinous fibres and in particular human keratinous fibres using aminoindoles in combination with an oxidizing system.

The invention also relates to the tinctorial compositions used in the course of this method, as well as to the device intended to be used in carrying out this method.

Further subjects of the invention will become apparent on reading the description and the examples which follow.

The method for dyeing keratinous fibres, and in particular human keratinous fibres such as hair, according to the invention, is essentially characterized in that a composition (A) containing, in a medium appropriate for dyeing, at least one aminoindole corresponding to the formula:

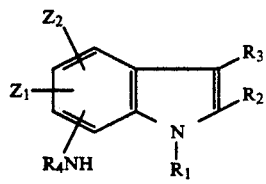

(I)

in which:

$R_1$ and $R_3$, independently of one another, represent a hydrogen atom or a $C_1-C_4$ alkyl group;

$R_2$ denotes hydrogen or a $C_1-C_4$ alkyl group or COOR′, R′ being a hydrogen atom or a $C_1-C_4$ alkyl group;

$R_4$ represents a hydrogen atom or a $C_1-C_4$ alkyl, $C_1-C_4$ hydroxyalkyl or $C_2-C_4$ polyhydroxyalkyl group;

$Z_1$ represents a hydrogen or halogen atom or a $C_1-C_4$ alkyl group or OR;

R being a hydrogen atom or a $C_1-C_4$ alkyl group; and $Z_2$ represents a hydrogen atom or a $C_1-C_4$ alkyl group;

and its salts is applied to said fibres, the colour being developed with the aid of an oxidizing system consisting of:

(i) iodide ions and hydrogen peroxide, the composition (A) in this case also containing either (a) iodide ions or (b) hydrogen peroxide and the application of the composition (A) being preceded or followed by the application of a composition (B) which contains, in a medium appropriate for dyeing, either:

(a) hydrogen peroxide at a pH of between 2 and 12 and preferably between 2 and 7, when the composition (A) contains iodide ions, or (b) iodide ions at a pH of between 3 and 11, when the composition (A) contains hydrogen peroxide;

(ii) nitrites, the application of the composition (A) being followed by the application of an aqueous composition (B) having an acid pH, the composition (A) or the composition (B) containing at least one nitrite;

(iii) oxidizing agents chosen from periodic acid and its water-soluble salts, sodium hypochlorite, potassium ferricyanide, silver oxide, Fenton's reagent, lead(IV) oxide, caesium sulphate and ammonium persulphate, these oxidizing agents being present in the composition (A) or being applied separately, at the same time or subsequently, by means of a composition (B) containing them in a medium appropriate for dyeing;

(iv) metal anions chosen from the permanganates or bichromates, these oxidizing agents being applied by means of an aqueous composition (B) having a pH of from 2 to 10, before the application of the composition (A);

(v) salts of metals of groups III to VIII of the periodic table, these metal salts being applied in a separate step by means of a composition (B) containing these salts in a medium appropriate for dyeing;

(vi) rare earth salts, these rare earth salts being applied by means of a composition (B) containing them in a medium appropriate for dyeing, the composition (B) being applied before or after the application of the composition (A).

According to the invention, the application of the compositions (A) and (B) is preferably separated by a rinsing.

Amongst the aminoindole derivatives corresponding to the formula (I), the following may be mentioned: 4-aminoindole, 5-aminoindole, 6-aminoindole, 7-aminoindole, 5-amino-6-methoxy-2,3-dimethylindole, 6-amino-5-methoxy-2,3-dimethylindole, 5-amino-6-hydroxy-2,3-dimethylindole, 5-hydroxy-6-amino-2,3-dimethylindole, 6-N-β-hydroxyethylaminoindole, 6-N-β-hydroxyethylamino-1-methylindole, 6-methylaminoindole, (5 or 6)-amino-N-methylindole, 2-carboxy-6-aminoindole, 4-amino-2,3-dimethylindole, 6-amino-2,3-dimethylindole, 7-amino-2,3-dimethylindole, 6-amino-3-ethyl-2-methylindole, 6-amino-3-methylindole, 6-amino-2-methylindole, 6-amino-2-ethoxycarbonylindole and 7-amino-3-ethyl-2-methylindole, 6-N-(β,γ-dihydroxypropyl)aminoindole, 2,3,4,5-tetramethyl-6-aminoindole, 2,3-dimethyl-5-chloro-6-aminoindole, 2,3-dimethyl-5-ethyl-6-aminoindole, 2,3,4-trimethyl-6-aminoindole, 2-methyl-5-hydroxy-6- aminoindole, 4-methylaminoindole, 4-amino-1-methylindole, 2,3-dimethyl-6-aminoindole, 2,3,7-trimethyl-6-aminoindole, 2,3,5-trimethyl-6-aminoindole and their salts.

The new compounds belonging to the formula (I) correspond to the formula (IA):

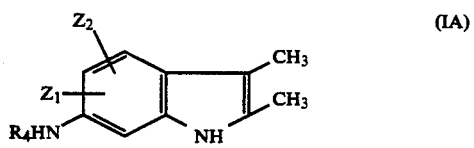

in which:
R$_4$ denotes hydrogen, C$_1$-C$_4$ alkyl, C$_1$-C$_4$ hydroxyalkyl or C$_2$-C$_4$ polyhydroxyalkyl;
Z$_1$ denotes hydrogen, alkyl or halogen; and
Z$_2$ denotes hydrogen or C$_1$-C$_4$ alkyl.
provided that at least one of the radicals Z$_1$ or Z$_2$ is other than hydrogen.

Amongst the new compounds, the following may be mentioned in particular: 2,3,7-trimethyl-6-aminoindole, 2,3,4,5-tetramethyl-6-aminoindole, 2,3-dimethyl-5-ethyl-6-aminoindole, 2,3-dimethyl-5-chloro-6-aminoindole and 2,3,4-trimethyl-6-aminoindole.

The compounds of formula (IA) in which R. denotes hydrogen are prepared in accordance with the following reaction scheme:

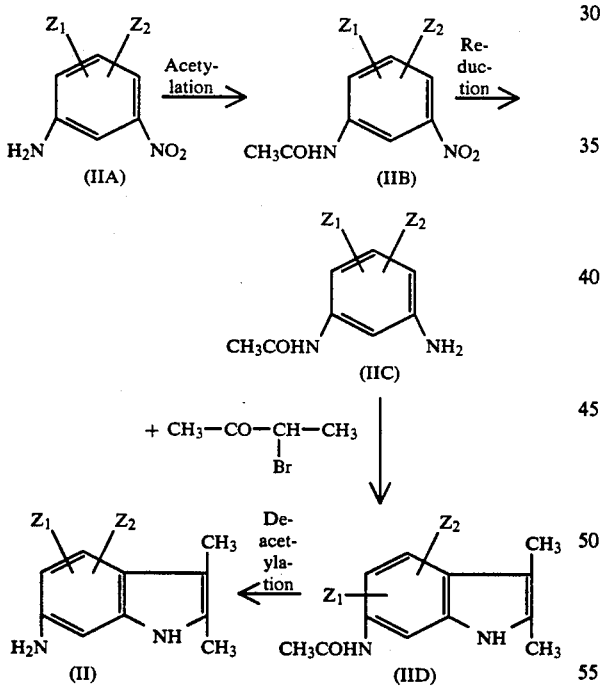

1ST STEP

It consists in an acetylation of the monosubstituted or disubstituted meta-nitroaniline of formula (IIA). The reaction concerned is a conventional acetylation using acetic anyhdride in a solvent, such as ethyl acetate, refluxing the solvent.

2ND STEP

The acetylated compound (IIB) is reduced in accordance with the conventional procedures. This reaction is effected either by iron/acetic acid in water at a temperature varying between 50° and 95° C. or by hydrogen transfer using, as catalyst, Pd/C in the presence of cyclohexane, in a solvent at a temperature between ambient temperature and the reflux temperature of the solvent (solvents which may be mentioned are lower C$_1$-C$_4$ alcohols), or by catalytic hydrogenation using Pd/C or Raney nickel as catalyst.

3RD STEP

The compound (IIC) is subjected to a condensation reaction with 3-bromobutan-2-one in dimethylformamide at a temperature between ambient temperature and 120° C.

4TH STEP

The compound (IID) is deacetylated in the presence of hot concentrated hydrochloric acid. The compounds (II) are thus obtained.

The compound (IA) in which R$_4$ is other than hydrogen is obtained from the compound (II) (R$_4$=H) by the methods for substitution of aromatic amines, in accordance with the reaction scheme:

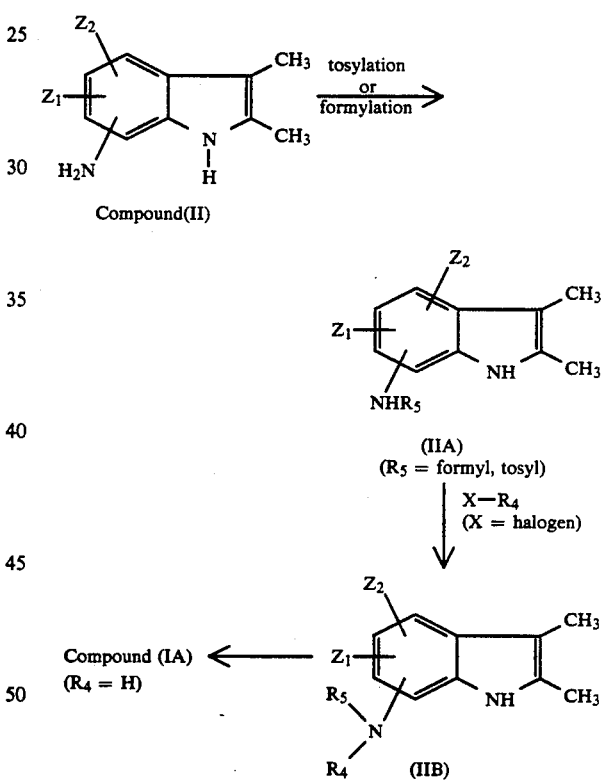

The compound (IIA) is obtained by formylation or tosylation. The compound (IIA) is subsequently alkylated by means of an alkyl halide X-R$_4$. When the alkyl halide is used in excess, a second group R$_4$ is introduced. The product (IA) is obtained by deformylation or detosylation of the compound (IIB).

Amongst the hydroxylation methods, those which may be mentioned are the action of β-chloroethyl chloroformate on the compound (II), which enables the corresponding β-chloroethyl carbamate to be obtained initially, which compound is subsequently subjected to the action of a strong inorganic base, enabling the compound (IA) for which the radical R$_4$ is a β-hydroxyethyl radical to be obtained.

According to a first variant of the invention, a composition (A) containing, in a medium appropriate for dyeing, at least one dye of formula (I) in combination with iodide ions is applied to the keratinous materials, the application of the composition (A) being preceded or followed by the application of a composition (B) which contains hydrogen peroxide in a medium appropriate for dyeing.

This method can also be carried out by applying to the keratinous fibres at least one composition (A) containing, in a medium appropriate for dyeing, the dye of formula (I) in combination with hydrogen peroxide, having a pH of between 2 and 7 and preferably between 3.5 and 7, the application of the composition (A) being preceded or followed by the application of a composition (B) which contains iodide ions, in a medium appropriate for dyeing.

The iodide ion in this variant of the method according to the invention is preferably chosen from alkali metal iodides, alkaline earth metal iodides or ammonium iodide and more particularly consists of potassium iodide.

The iodide ions are present in the compositions (A) or (B) in proportions of generally between 0.007 and 4% by weight, expressed as $I^-$ ions, and preferably between 0.08 and 1.5% by weight relative to the total weight of the composition (A) or (B).

According to a second variant of the invention, the method can be carried out using a nitrite as oxidizing agent to develop the colouring. The nitrites more particularly usable according to the invention are:
- alkali metal nitrites, alkaline earth metal nitrites or ammonium nitrite or nitrites of any other cation which is cosmetically acceptable when it is used for dyeing living human hair;
- organic derivatives of nitrites, such as, for example, amyl nitrite;
- nitrite carriers, that is to say compounds which by conversion give rise to a nitrite of the type defined above.

The particularly preferred nitrites are sodium nitrite, potassium nitrite or ammonium nitrite This variant of the method is carried out by applying to the keratinous materials the composition (A) based on the dye of formula (I) defined above and then an aqueous acid composition (B), the composition (A) or (B) containing at least one nitrite.

The nitrites are generally used in proportions of between 0.02 and 1 mole/liter.

According to a third variant of the invention, the oxidizing agents chosen from periodic acid and its water-soluble salts, sodium hypochlorite, potassium ferricyanide, silver oxide, Fenton's reagent, lead(IV) oxide, caesium sulphate and ammonium persulphate are preferably applied to the fibres by means of a composition (B) and after the application of the composition (A).

The particularly preferred oxidizing agents of this group are periodic acid and its water-soluble salts, such as the lithium, sodium, potassium, rubidium, caesium, magnesium, calcium, strontium, manganese, iron, copper, zinc and aluminium salts, the sodium and potassium salts being particularly preferred.

These oxidizing agents are present in proportions sufficient to develop a colouring, preferably between 0.004 mole and 0.07 mole and in particular between 0.01 mole and 0.04 mole per 100 g of composition.

According to a fourth variant of the invention, a composition containing, in a medium appropriate for dyeing, at a pH of between 2 and 10, an anion of a metal having a good affinity for keratin and having an oxidation-reduction potential higher than that of the compounds of formula (I) is initially applied to the keratinous fibres. This anion is preferably chosen from the permanganates or the bichromates and more particularly potassium permanganate and sodium bichromate.

Subsequently a composition containing, in a medium appropriate for dyeing, at a pH between 4 and 10, a dye corresponding to the formula (I) defined above is applied.

These metal anions are generally used in molar amounts of anions of more than $10^{-3}$ moles/1,000 g up to preferably 1 mole/1,000 g. The compositions containing the anions must not contain organic agents having a reducing effect thereon.

According to a fifth variant of the invention, oxidation catalysts are used chosen from metal salts, such as manganese, cobalt, iron, copper and silver salts. Manganese sulphate, manganese lactate, cobalt chloride, ferric chloride, cupric chloride and ammoniacal silver nitrate may be mentioned by way of example. The preferred salts are the copper salts. These salts are used in proportions of 0.01 to 2%, expressed as metal ion.

According to this variant, the keratinous fibres, and in particular the hair, are (is) brought into contact with a composition (B) containing the metal salt in a medium appropriate for dyeing, before or after the application of the composition (A) containing the compound of formula (I) and rinsing is preferably carried out between the two steps.

The preferred embodiment consists in applying a cupric salt initially and the composition (A) subsequently.

This dyeing may be followed, after rinsing, by the application of a solution of hydrogen peroxide to lighten the colour obtained if necessary.

According to a sixth variant, rare earth salts are used. The rare earth salts which can be used according to the invention are chosen from the salts of lanthanides, and in particular the cerium $Ce^{+3}$ and $C^{-4+}$, lanthanum $La^{3+}$, europium $Eu^{2+}$ and $Eu^{3+}$, gadolinium $Gd^{3+}$, ytterbium $Yb^{2+}$ and $Yb^{3+}$ and dysprosium $Dy^{3+}$ salts. The preferred salts are, in particular, the sulphates, chlorides or nitrates.

These rare earth salts are present in proportions of between 0.1 and 8% by weight relative to the total weight of the composition.

Cerium $Ce^{3+}$ and $Ce^{4+}$ salts in the form of sulphates and chlorides are preferably used.

When compositions based on hydrogen peroxide are used, the hydrogen peroxide content is generally between 1 and 40 volumes and preferably between 2 and 10 volumes and more particularly between 3 and 10 volumes.

According to another embodiment, a tinctorial composition containing, in a cosmetically acceptable aqueous medium having a pH of less than or equal to 7, at least one indole derivative corresponding to the formula:

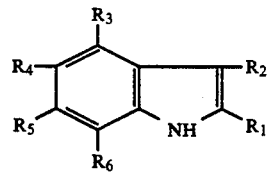

(II)

in which:
- $R_1$ and $R_2$, which may be identical or different, denote H or $CH_3$;
- $R_3$ denotes H, $NH_2$, OH or $-OCH_3$;
- $R_4$ denotes H, $NH_2$, OH or $-OC_2H_5$;
- $R_5$ denotes H, $NH_2$, OH or $-NHCH_2CH_2OH$; and
- $R_6$ denotes H or OH;

at least two of the radicals $R_3$, $R_4$, $R_5$ and $R_6$ denoting hydrogen,
and at least one and one only of the groups $R_3$, $R_4$ or $R_5$ denoting $NH_2$, or $-NHCH_2CH_2OH$ for $R_5$; and when $R_5$ denotes an amino group and $R_4$ a, OH group, $R_1$ and $R_2$ denote $CH_3$, and the salts of corresponding acids, is applied initially.

After an exposure time followed by rinsing and drying, an alkaline oxidizing solution is subsequently applied, this application being followed by rinsing and shampooing.

The Applicant has found that this method enabled varied hues having glints or natural light to dark blond, copper and dark auburn hues to be obtained which were uniform even after several superpositions and covered the hair well.

The more particularly preferred dyes in this embodiment are chosen from 4-aminoindole, 5-aminoindole, 6-aminoindole, 6-amino-2,3-dimethyl-5-hydroxyindole and 6-β-hydroxyethylaminoindole.

The amount of aminoindoles corresponding to the formula (I) used in the composition (A), according to the invention, is generally in proportions of between 0.01 and 5% by weight relative to the total weight of the composition, and preferably between 0.03 and 2.5% by weight.

The compositions which can be used according to the invention can be in various forms, such as in the form of lotions, thickened to a greater or lesser extent, creams, foams and gels. These compositions may also be provided in multi-compartment devices or kits containing the various components intended to be mixed at the time of use, or in the form of aerosols.

The compositions which can be used in the method according to the invention and which are also a subject of the invention are characterized in that they contain, in a medium appropriate for dyeing, at least one aminoindole derivative of formula (I) and at least iodide ions or nitrites, as defined above.

The proportions of the various constituents are as defined above.

The medium appropriate for dyeing is preferably an aqueous medium which must be cosmetically acceptable when the compositions are intended for dyeing living human hair. This aqueous medium can consist of water or of a water/solvent(s) mixture.

The solvents are chosen from the organic solvents and preferentially from ethyl alcohol, propyl alcohol or isopropyl alcohol, tertiary butyl alcohol, ethylene glycol, ethylene glycol monomethyl, monoethyl and monobutyl ethers, ethylene glycol monoethyl ether-acetate, propylene glycol, propylene glycol and dipropylene glycol monomethyl ethers, and methyl lactate.

The particularly preferred solvents are ethyl alcohol, propylene glycol and ethylene glycol monobutyl ether.

According to another embodiment, the medium appropriate for dyeing can consist of anhydrous solvents, such as those defined preferentially above, the composition in this case being either mixed at the time of use with an aqueous medium or applied to the keratinous fibres previously wetted with an aqueous composition. According to the invention, a medium containing less than 1% of water is termed an anhydrous solvent medium.

When the medium appropriate for dyeing is aqueous, the pH of the composition (A) is preferably between 2 and 7 and in particular between 3.5 and 7.

When the medium appropriate for dyeing consists of a water/solvent(s) mixture, the solvents are used in concentrations of between 0.5 and 75% by weight, relative to the total weight of the composition, preferably between 2 and 50% and more particularly between 2 and 20% by weight.

In addition to the indole dye corresponding to the formula (I) or (II) above, the colouring composition can contain other indoles, amongst which 2-methyl-5,6-dihydroxyindole and its corresponding acid addition salt, 5,6-dihydroxyindole and 5,6-dihydroxy-2-carboxyindole may be mentioned.

The compositions according to the invention may contain any other adjuvants customarily used for dyeing keratinous fibres and in particular cosmetically acceptable adjuvants, to the extent that these compositions are applied for dyeing living human hair.

In this latter case, the compositions may contain, in particular, fatty amides in preferential proportions of 0.05 to 10% by weight, anionic, cationic, nonionic or amphoteric surfactants or their mixtures, preferably present in proportions of between 0.1 and 50% by weight, thickeners, perfumes, sequestering agents, film-forming agents, treatment agents, dispersing agents, conditioning agents, preservatives, opacifying agents and swelling agents for keratinous fibres The thickeners are chosen from sodium alginate, gum arabic, guar gum, heterobiopolysaccharides, such as xanthan gum, scleroglucans, cellulose derivatives, such as methylcellulose, hydroxyethylcellulose, hydroxypropylmethylcellulose and the sodium salt of carboxymethylcellulose and preferentially crosslinked acrylic acid polymers.

Inorganic thickeners may also be used, such as bentonite. These thickeners are used on their own or as a mixture and are preferably present in proportions of between 0.1 and 5% by weight relative to the total weight of the composition, and advantageously between 0.5 and 3% by weight.

The alkalinising agents which may be used in the compositions can be, in particular, amines, such as alkanolamines, alkylamines, alkali metal hydroxides or carbonates or ammonium hydroxide or carbonate.

The acidifying agents which may be used in these compositions may be chosen from lactic acid, acetic acid, tartaric acid, phosphoric acid, hydrochloric acid and citric acid.

It is, of course, possible to use any other acceptable alkalinizing or acidifying agent, in particular in the case of cosmetic dyeing of the hair.

When the compositions are used in the form of foam, they may be packaged under pressure and in an aerosol device in the presence of a propellant and at least one foam generator.

The foam generators may be anionic, cationic, non-ionic or amphoteric foaming polymers, or their mixtures, or surfactants of the type of those defined above.

In the embodiment using the dyes of formula (II), the oxidizing composition preferably consists of an aqueous solution of oxidizing agent which is mixed at the time of use with an alkaline aqueous solution which may contain solvents and surfactants.

The oxidizing agent is chosen from hydrogen peroxide, urea peroxide and per salts such as alkali metal or ammonium percarbonates and perborates.

The alkaline agents are chosen from ammonia and alkanolamines such as 2-amino-2-methylpropan-1-ol, monoethanolamine, monomethylethanolamine or dimethylethanolamine.

The aqueous solution of oxidizing agent can contain solvents of the type defined above, surfactants and also self-emulsifiable waxes or polyoxyethylenated alcohols for thickening these solutions.

The proportion of oxidizing agent in the compositions is between 1 and 15% by weight relative to the total weight of the oxidizing composition, and preferably between 1 and 8%.

The proportion of oxidizing agent in the alkaline oxidizing compositions which are applied to the hair is between 1 and 10% by weight relative to the total weight of the composition, and preferably between 1 and 5%.

The pH of the oxidizing composition is between 8.5 and 12.

The invention also relates to an agent for dyeing keratinous fibres and in particular human keratinous fibres, containing several components, one of which components consists of the composition (A) defined above and the other component consists of one of the compositions (B) also defined above, the respective components being chosen in accordance with the various variants described above.

Another subject of the invention is a multicompartment device also termed "dyeing kit" or "dyeing set" comprising all the components intended to be applied to the keratinous fibres for a given dyeing, in successive applications with or without premixing, as mentioned above.

Devices of this type are known per se and can comprise a first compartment containing the composition (A), comprising the aminoindole derivative of formula (I) in a medium appropriate for dyeing, and, in a second compartment, a composition (B) defined above.

When the medium containing the aminoindole derivative of formula (I) is anhydrous, a third compartment can be provided containing an aqueous medium appropriate for dyeing and intended to be mixed before use with the composition in said first compartment.

The multicompartment devices which can be used according to the invention can be fitted with means of mixing at the time of use and their contents can be packaged under an inert atmosphere.

The method and the compositions used, according to the invention, can be employed for dyeing natural or already dyed hair which may or may not have been given a permanent wave or may or may not have been straightened, or strongly or slightly bleached hair, which may have been given a permanent wave. It is also possible to use them for dyeing fur or wool.

The examples which follow are intended to illustrate the invention without any restriction being implied.

PREPARATION EXAMPLE 1

Preparation of 6-N-$\beta$-hydroxyethylaminoindole

Step 1

Preparation of 6-N-($\beta$-chloroethoxycarbonyl)aminoindole 0.05 mol (6.6 g) of 6-aminoindole and 5.5 g of calcium carbonate in 30 ml of dioxane are heated to reflux. 0.055 mol (7.9 g) of $\beta$-chloroethyl chloroformate is added little by little. The reaction mixture is diluted with ice. The expected product precipitates. It melts at 134° C.

Analysis of the product recrystallized from ethanol gives the following results:

| | Analysis for $C_{11}H_{11}N_2O_2Cl$ | | | | |
|---|---|---|---|---|---|
| | C | H | Cl | O | N |
| Calculated | 55.36 | 4.65 | 14.85 | 13.41 | 11.74 |
| Found | 55.40 | 4.68 | 14.72 | 13.27 | 11.67 |

Step 2

Preparation of 6-N-$\beta$-hydroxyethylaminoindole 28 mol (66.5 g) of 6-N-($\beta$-chloroethoxycarbonyl)aminoindole is added to 200 ml of 4 N sodium hydroxide solution and 66.5 ml of ethanol. The reaction mixture is heated under reflux for 1 hour. The expected product is precipitated by adding ice. It melts at 99° C.

Elementary analysis of the product obtained gives the following results:

| | Analysis for $C_{10}H_{12}N_2O$ | | | |
|---|---|---|---|---|
| | C | H | N | O |
| Calculated | 68.16 | 6.86 | 15.90 | 9.08 |
| Found | 67.88 | 6.91 | 15.91 | 9.15 |

PREPARATION EXAMPLE 2

Preparation of 6-N-($\beta$-hydroxyethyl)amino-1-methylindole hydrochloride

Step 1

Preparation of N-(6-indolyl)-1,3-oxazolidin-2-one 60 ml of methanol are added to 120 ml of a 30% solution of sodium methylate in methanol and 0.25 mol (60 g) of 6-($\beta$-chloroethoxycarbonyl)aminoindole (prepared in accordance with the first step of Example 1) are then added, with stirring. The temperature reaches 50° C. Stirring is continued for 15 minutes after the end of the addition. The precipitate formed is drained, washed with alcohol and then dried. It melts at 199° C.

Analysis of the product recrystallized from acetic acid gives the following results:

| | Analysis for $C_{11}H_{10}N_2O_2$ | | | |
|---|---|---|---|---|
| | C | H | N | O |
| Calculated | 65.34 | 4.98 | 13.85 | 15.82 |
| Found | 65.42 | 5.02 | 13.75 | 15.86 |

Step 2

Preparation of N-6-(1-methyl)indolyl-1,3-oxazolidin-2-one 100 ml of a 30% solution of sodium methylate in methanol are added to a solution of 0.15 mol (30.5 g) of N-(6-indolyl)-1,3-oxazolidin-2-one in 300 ml of dimethylformamide. The reaction mixture is heated to 40° C. 28 ml of methyl iodide are added dropwise. Heating is continued for 1 hour after the end of the addition. After dilution of the reaction mixture with ice-water, the expected product precipitates. After draining and washing with water and then with ethanol, it melts at 160° C.

Analysis of the product recrystallized from acetic acid gives the following results:

|  | Analysis for $C_{12}H_{12}N_2O_2$ | | | |
|---|---|---|---|---|
|  | C | H | N | O |
| Calculated | 66.65 | 5.59 | 12.95 | 14.80 |
| Found | 66.55 | 5.62 | 12.76 | 15.08 |

Step 3

Preparation of 6-(β-hydroxyethyl)amino-1-methylindole hydrochloride 0.02 mol (4.32 g) of N-[6-(1-methyl)indolyl]-1,3-oxazolidin-2-one in 17 ml of 4 N sodium hydroxide solution to which 2 ml of ethanol have been added is heated under reflux for 1 hour. The reaction mixture is diluted with ice-water and the product obtained is then extracted with ethyl acetate.

The oil obtained after evaporation of the ethyl acetate is added to 7 ml of a 7M hydrochloric acid solution in ethanol. The expected product precipitates.

Analysis of the product obtained after washing and drying gives the following results:

|  | Analysis for $C_{11}H_{15}ClN_2O$ | | | | |
|---|---|---|---|---|---|
|  | C | H | Cl | N | O |
| Calculated | 58.28 | 6.67 | 15.64 | 12.36 | 7.06 |
| Found | 58.16 | 6.70 | 15.52 | 12.45 | 7.13 |

PREPARATION EXAMPLE 3

Preparation of 6-amino-2,3,4-trimethylindole hydrochloride

Step 1

Preparation of 3-methyl-5-nitroacetanilide 9 g of acetic anhydride are added dropwise to a solution of 12.2 g of 3-methyl-5-nitroaniline in 36 ml of ethyl acetate under reflux. After refluxing for 30 minutes, the mixture is cooled, the precipitate is drained and washed with ethyl acetate (10 ml) and the product is dried. 15.2 g of expected product are obtained.

Analysis of the product recrystallized from ethanol gives the following results:
m.p.=185° C.

|  | Analysis for $C_9H_{10}N_2O_3$ | | | |
|---|---|---|---|---|
|  | C | H | N | O |
| Calculated | 55.67 | 5.19 | 14.43 | 24.72 |
| Found | 55.66 | 5.20 | 14.40 | 24.83 |

Step 2

Preparation of 3-acetamido-5-methylaniline 40 ml of ethanol, 25 ml of cyclohexene and then 12.6 g of 3-methyl-5-nitroacetanilide are added to 2.6 g of 10% Pd/C wetted with 2.6 g of water. After refluxing for 2 hours, the suspension is filtered hot and the solid is washed with ethanol (50 ml). The filtrate is evaporated to dryness under vacuum. 10 g of white precipitate are obtained.

Analysis of the product recrystallized from ethyl acetate gives the following results:
m.p.=123° C.

|  | Analysis for $C_9H_{12}N_2O$ | | | |
|---|---|---|---|---|
|  | C | H | N | O |
| Calculated | 65.83 | 7.37 | 17.06 | 9.74 |
| Found | 65.40 | 7.35 | 16.94 | 10.69 |

Step 3

Preparation of 6-acetamido-2,3,4-trimethylindole 9 g of 3-acetamido-5-methylaniline are dissolved in 20 ml of dimethylformamide and 3.2 ml of 3-bromobutan-2-one are then added. The mixture is left at ambient temperature for 1 hour and the temperature is then raised to 100°–110° C. for one hour. The mixture is cooled and poured into 100 ml of ice-water. The precipitate is drained and washed successively with 50 ml of distilled water, 20 ml of ethanol and 20 ml of isopropyl ether. 4.2 g of white precipitate are obtained.

Analysis of the product recrystallized from acetic acid gives the following results:
m.p.=255° C.

|  | Analysis for $C_{13}H_{16}N_2O$ | | | |
|---|---|---|---|---|
|  | C | H | N | O |
| Calculated | 72.19 | 7.46 | 12.95 | 7.40 |
| Found | 71.04 | 7.52 | 12.73 | 8.42 |

Step 4

Preparation of 6-amino-2,3,4-trimethylindole

A suspension of 3.67 g of 6-acetamido-2,3,4-trimethylindole in 15 ml of hydrochloric acid (12N) is brought to 100° C. for 3 hours. The mixture is cooled and the precipitate is drained and washed successively with 3 ml of hydrochloric acid (12N) and 20 ml of absolute ethanol. 3.5 g of a white precipitate are obtained.

Analysis of the product gives the following results:

|  | Analysis for $C_{11}H_{15}ClN_2$ | | | |
|---|---|---|---|---|
|  | C | H | Cl | N |
| Calculated | 62.70 | 7.18 | 16.83 | 13.29 |
| Found | 62.72 | 7.24 | 17.09 | 13.22 |

PREPARATION EXAMPLE 4

Preparation of 6-amino-2,3,7-trimethylindole hydrochloride

Step 1

Preparation of 2-methyl-3-nitroacetanilide

The procedure is carried out in a manner identical to that in step 1 of Example 3, using 2-methyl-3-nitroaniline as the starting material.

Analysis of the product recrystallized from ethanol gives the following results:

m.p.=146° C. repeatedly then 162° C.

| | Analysis for $C_9H_{10}N_2O_3$ | | | |
|---|---|---|---|---|
| | C | H | N | O |
| Calculated | 55.67 | 5.19 | 14.43 | 24.72 |
| Found | 55.72 | 5.27 | 14.42 | 24.97 |

Step 2

Preparation of 2-methyl-3-acetamidoaniline

The procedure is carried out in a manner identical to that in step 2 of Example 3.

Analysis of the product recrystallized from a mixture of ethyl acetate/ethanol (5/2) gives the following results:

m.p.=145° C.

| | Analysis for $C_9H_{12}N_2O$ | | | |
|---|---|---|---|---|
| | C | H | N | O |
| Calculated | 65.83 | 7.37 | 17.06 | 9.74 |
| Found | 65.76 | 7.44 | 17.18 | 9.71 |

Step 3

Preparation of 6-acetamido-2,3,7-trimethylindole

The procedure is carried out in a manner identical to that in step 3 of Example 3.

Analysis of the product recrystallized from acetic acid gives the following results:

m.p.=242° C.

| | Analysis for $C_{13}H_{16}N_2O$ | | | |
|---|---|---|---|---|
| | C | H | N | O |
| Calculated | 72.19 | 7.46 | 12.95 | 7.40 |
| Found | 72.16 | 7.46 | 12.88 | 7.25 |

Step 4

Preparation of 6-amino-2,3,7-trimethylindole hydrochloride

The procedure is carried out in a manner identical to that in step 4 of Example 3.

Analysis of the product gives the following results:

| | Analysis for $C_{11}H_{15}ClN_2$ | | | |
|---|---|---|---|---|
| | C | H | Cl | N |
| Calculated | 62.70 | 7.18 | 16.83 | 13.29 |
| Found | 62.72 | 7.18 | 17.02 | 13.31 |

PREPARATION EXAMPLE 5

Preparation of 6-amino-2,3,4,5-tetramethylindole hydrochloride

Step 1

Preparation of 2,3-dimethyl-5-nitroacetanilide

The procedure is carried out in a manner identical to that in step 1 of Example 3, using 2,3-dimethyl-5-nitroaniline as the starting material.

Analysis of the product recrystallized from ethanol gives the following results:

m.p.=230° C.

| | Analysis for $C_{10}H_{12}N_2O_3$ | | | |
|---|---|---|---|---|
| | C | H | N | O |
| Calculated | 57.69 | 5.81 | 13.45 | 23.05 |
| Found | 57.77 | 5.90 | 13.40 | 23.12 |

Step 2

Preparation of 3-acetamido-4,5-dimethylaniline

The procedure is carried out in a manner identical to that in step 2 of Example 3.

Analysis of the product recrystallized from ethanol gives the following results:

m.p.=162° C.

| | Analysis for $C_{10}H_{14}N_2O$ | | | |
|---|---|---|---|---|
| | C | H | N | O |
| Calculated | 67.39 | 7.92 | 15.72 | 8.98 |
| Found | 67.38 | 7.98 | 15.63 | 9.08 |

Step 3

Preparation of 6-acetamido-2,3,4,5-tetramethylindole

The procedure is carried out in a manner identical to that in step 3 of Example 3.

Analysis of the product recrystallized from acetic acid gives the following results:

m.p.=265° C.

| | Analysis for $C_{14}H_{18}N_2O$ | | | |
|---|---|---|---|---|
| | C | H | N | O |
| Calculated | -73.01 | 7.88 | 12.16 | 6.95 |
| Found | 72.93 | 7.87 | 12.19 | 7.07 |

Step 4

Preparation of 6-amino-2,3,4,5-tetramethylindole hydrochloride

The procedure is carried out in a manner identical to that in step 4 of Example 3.

Analysis of the product gives the following results:

| | Analysis for $C_{12}H_{17}ClN_2$ | | | |
|---|---|---|---|---|
| | C | H | Cl | N |
| Calculated | 64.13 | 7.62 | 15.78 | 12.47 |
| Found | 64.03 | 7.71 | 15.83 | 12.50 |

PREPARATION EXAMPLE 6

Preparation of 6-amino-2,3,-dimethyl-5-ethylindole hydrochloride

Step 1

Preparation of 2-ethyl-5-nitroacetanilide

The procedure is carried out in a manner identical to that in step 1 of Example 3, using 2-ethyl-5-nitroaniline as the starting material.

Analysis of the product recrystallized from ethanol gives the following results:
m.p.=158° C.

|  | Analysis for $C_{10}H_{12}N_2O_3$ | | | |
|---|---|---|---|---|
|  | C | H | N | O |
| Calculated | 57.69 | 5.81 | 13.45 | 23.05 |
| Found | 57.63 | 5.82 | 13.43 | 22.98 |

Step 2

Preparation of 3-acetamido-4-ethylaniline

The procedure is carried out in a manner identical to that in step 2 of Example 3.

Analysis of the product recrystallized from ethanol gives the following results:
m.p.=150° C.

|  | Analysis for $C_{10}H_{14}N_2O$ | | | |
|---|---|---|---|---|
|  | C | H | N | O |
| Calculated | 67.39 | 7.92 | 15.72 | 8.98 |
| Found | 67.44 | 7.93 | 15.89 | 9.06 |

Step 3

Preparation of 6-acetamido-2,3-dimethy-5-ethylindole

The procedure is carried out in a manner identical to that in step 3 of Example 3.

Analysis of the product recrystallized from acetic acid gives the following results:
m.p.=251° C.

|  | Analysis for $C_{14}H_{18}N_2O$ | | | |
|---|---|---|---|---|
|  | C | H | N | O |
| Calculated | 73.01 | 7.88 | 12.16 | 6.95 |
| Found | 72.02 | 7.88 | 12.07 | 6.97 |

Step 4

Preparation of 6-amino-2,3-dimethyl-5-ethylindole hydrochloride

The procedure is carried out in a manner identical to that in step 4 of Example 3.

Analysis of the product gives the following results:

|  | Analysis for $C_{12}H_{17}ClN_2$ | | | |
|---|---|---|---|---|
|  | C | H | Cl | N |
| Calculated | 64.13 | 7.62 | 15.78 | 12.47 |
| Found | 73.97 | 7.70 | 15.58 | 12.55 |

PREPARATION EXAMPLE 7

Preparation of 6-amino-5-chloro-2,3-dimethylindole hydrochloride

Step 1

Preparation of 2-chloro-5-nitroacetanilide

The procedure is carried out in a manner identical to that in step 1 of Example 3, using 2-chloro-5-nitroaniline as the starting material.

Analysis of the product recrystallized from ethanol gives the following results:
m.p.=157° C.

|  | Analysis for $C_8H_7ClN_2O_3$ | | | | |
|---|---|---|---|---|---|
|  | C | H | Cl | N | O |
| Calculated | 44.77 | 3.29 | 16.52 | 13.05 | 22.37 |
| Found | 44.87 | 3.30 | 16.44 | 13.10 | 22.24 |

Step 2

Preparation of 3-acetamido-4-chloroaniline

A suspension of 345 g of iron in a mixture of 850 ml of water and 20 ml of acetic acid is brought to 90° C. and 172.5 g of 2-chloro-5-nitroacetanilide are added in the course of 45 minutes. After 10 minutes at 95° C., the mixture is cooled and the ferric sludge is filtered off and washed three times with 1 liter of acetone. The filtrate is evaporated to dryness to give 112 g of white precipitate.

Analysis of the product recrystallized from acetone gives the following results:
m.p.=198° C.

|  | Analysis for $C_8H_9ClN_2O$ | | | | |
|---|---|---|---|---|---|
|  | C | H | Cl | N | O |
| Calculated | 52.05 | 4.91 | 19.2 | 15.17 | 8.67 |
| Found | 52.10 | 4.94 | 19.45 | 15.24 | 8.78 |

Step 3

Preparation of 6-acetamido-5-chloro-2,3-dimethylindole

The procedure is carried out in a manner identical to that in step 3 of Example 3.

Analysis of the product recrystallized from acetic acid gives the following results:
m.p.=264° C.

|  | Analysis for $C_{12}H_{13}ClN_2O$ | | | | |
|---|---|---|---|---|---|
|  | C | H | Cl | N | O |
| Calculated | 60.89 | 5.54 | 14.98 | 11.83 | 6.76 |
| Found | 60.78 | 5.53 | 15.15 | 11.86 | 6.77 |

Step 4

Preparation of 6-amino-5-chloro-2,3-dimethylindole hydrochloride

The procedure is carried out in a manner identical to that in step 4 of Example 3.

Analysis of the product gives the following results:

| Analysis for $C_{10}H_{12}ClN_2O$ | | | |
|---|---|---|---|
| | C | H | Cl | N |
| Calculated | 51.97 | 5.23 | 30.68 | 12.12 |
| Found | 52.00 | 5.29 | 30.63 | 11.88 |

PREPARATION EXAMPLE 8

Preparation of 6-N-(β-γ-dihydroxypropyl)aminoindole 26.4 g of 6-aminoindole are dissolved in 70 ml of absolute alcohol. 29.6 g of glycidol are added and the mixture is stirred for 4 hours at 30°–40° C.

The mixture is poured into 200 g of ice-water and extracted with 3 times 100 ml of ethyl acetate. The solvent is washed with water. It is dried over $Na_2SO_4$ and driven off to dryness under vacuum.

The oily residue is taken up three times in 0.6 liter of isopropyl ether under reflux. The mixture is filtered and the ether is driven off to dryness under vacuum; the residual oil is taken up in 10 cc of ethyl acetate and the product is purified on a silica column (eluent ethyl acetate 9/heptane 1). The fraction containing the expected product is evaporated to dryness under vacuum. A colourless oil is obtained which gives the following results:

| Analysis for $C_{11}H_{14}N_2O_2$ | | | | |
|---|---|---|---|---|
| Calculated | C = 64.06 | H = 6.84 | N = 13.58 | O = 15.51 |
| Found | C = 63.95 | H = 6.98 | N = 13.48 | O = 15.59 |

EXAMPLES 1 TO 4

The following compositions are prepared

| | |
|---|---|
| Indole dye | xg |
| potassium iodide | yg |
| ethyl alcohol | 10.0 g |
| guar gum, sold under the name JAGUAR BP60 by MEYHALL | 1.0 g |
| glycoside alkyl ether sold in 60% AS concentration under the name TRITON CG110 by ROHM & HAAS | 5.0 g AS |
| preservative | 0.6 g |
| demineralized water qs | 100.0 g |

The pH is adjusted to the value indicated in the table by adding alkalinizing or acidifying agent, termed "pH agent".

| EXAMPLE | COMPOUND | x | y | pH AGENT | pH |
|---|---|---|---|---|---|
| 1 | 6-aminoindole | 1.0 | 0.9 | citric acid | 6.5 |
| 2 | 7-aminoindole | 1.0 | 0.9 | triethanolamine | 6.5 |
| 3 | 4-aminoindole | 0.6 | 0.4 | citric acid | 6.5 |
| 4 | 5-aminoindole | 0.5 | 0.45 | citric acid | 6.5 |

Compositions 1 to 4 are applied for 15 minutes to grey hair which is 90% white. After intermediate rinsing, an oxidizing milk at pH 3 assaying at 12.5 volume hydrogen peroxide is applied for 5 minutes. The hair is rinsed again and final shampooing is carried out. The hair is dried.

The hues obtained are as follows:

| COMPOSITION | COLOURS |
|---|---|
| 1 | chestnut |
| 2 | very light, slightly ashy blonde |
| 3 | very light, slightly ashy blonde |
| 4 | light pearly blonde |

EXAMPLES 5 AND 6

The following compositions are prepared:

| | |
|---|---|
| indole dye | 1.0 g |
| potassium iodide | 0.5 g |
| ethylene glycol monobutyl ether | z1 g |
| nonylphenol containing 9 moles of ethylene oxide, sold under the name SINNOPAL NP9 by HENKEL | z2 g |
| demineralized water qs | 100.0 g |

| EXAMPLE | COMPOUND | Z1 | Z2 | pH AGENT | pH |
|---|---|---|---|---|---|
| 5 | 2,3-dimethyl-5-amino-6-methoxyindole hydrochloride | 10.0 | 2.5 | triethanolamine | 5.5 |
| 6 | 2,3-dimethyl-5-methoxy-6-aminoindole | 17.5 | 5.0 | lactic acid | 7.0 |

Compositions 5 and 6 are applied under the same conditions as compositions 1 to 4.

The hues obtained are as follows:

| COMPOSITION | COLOURS |
|---|---|
| 5 | natural golden blonde with a curly tendency |
| 6 | light pearly blonde |

EXAMPLE 7

| | |
|---|---|
| 6-aminoindole | 1.0 g |
| ethyl alcohol | 10.0 g |
| potassium iodide | 1.0 g |
| guar gum derivative sold under the name JAGUAR HP 60 by MEYHALL | 1.0 g |
| glycoside alkyl ether sold under the name TRITON CG 110 by ROHM & HAAS | 5.0 g AS |
| preservatives qs | |
| spontaneous | pH = 7.1 |
| demineralized water qs | 100.0 g |

This composition is applied for 15 minutes to grey hair which is 90% white. After rinsing, an oxidizing milk at pH 3 assaying at 12.5 volume hydrogen peroxide is applied for 5 minutes. The hair is rinsed, shampooing is carried out and the hair is dried. A deep chestnut colouring is finally obtained.

EXAMPLE 8

| COMPOSITION (A) | |
|---|---|
| 6-aminoindole | 0.5 g |
| ethylene glycol monobutyl ether | 12.0 g |
| nonylphenol containing 9 moles of ethylene oxide, sold under the name SINNOPAL NP 9 by HENKEL | 20.0 g |
| citric acid qs | pH = 5.2 |
| demineralized water qs | 100.0 g |
| COMPOSITION (B) | |
| sodium metaperiodate | 3.5 g |

-continued

| | |
|---|---|
| ethyl alcohol | 5.0 g |
| citric acid qs | pH = 4.0 |
| demineralized water qs | 100.0 g |

Composition (A) is applied for 20 minutes to grey hair which is 90% white. The hair is rinsed and composition (B) is then applied for 15 minutes. The hair is rinsed again. After drying, a deep ashy blonde colouring is finally obtained.

EXAMPLE 9

| COMPOSITION (A) | |
|---|---|
| 6-aminoindole | 1.5 g |
| ethyl alcohol | 6.5 g |
| propylene glycol | 2.0 g |
| nonylphenol containing 9 moles of ethylene oxide sold under the name SINNOPAL NP 9 by HENKEL | 14.0 g |
| citric acid qs | pH = 4.5 |
| demineralized water qs | 100.0 g |
| COMPOSITION (B) | |
| sodium nitrite | 2.0 g |
| hydrochloric acid qs | pH = 3.8 |
| demineralized water qs | 100.0 g |

Composition (A) is applied for 20 minutes to grey hair which is 90% white. The hair is rinsed and composition (B) is then applied for 5 minutes. The hair is rinsed and dried. The hair is then dyed in a deep coppery golden blonde hue.

EXAMPLE 10

| COMPOSITION (A) | |
|---|---|
| potassium permanganate | 0.40 g |
| hydrochloric acid qs | pH = 3.0 |
| demineralized water qs | 100.0 g |
| COMPOSITION (B) | |
| 6-aminoindole | 2.0 g |
| ethylene glycol monoethyl ether | 12.0 g |
| polyethylene glycol of MW = 280 | 15.0 g |
| citric acid qs | pH = 5.0 |
| demineralized water qs | 100.0 g |

Composition (A) is applied for 15 minutes to grey hair which is 90% white. The hair is rinsed and composition (B) is then applied for 20 minutes. The hair is rinsed again and dried. The final colouring obtained is a natural light chestnut.

EXAMPLE 11

| COMPOSITION (A) | |
|---|---|
| copper sulphate containing 5 moles of water | 1.0 g |
| sodium lauryl ether-sulphate containing 2 moles of ethylene oxide, sold under the name SACTIPON 8533 by LEVER | 5.0 g AS |
| hydroxyethyl cellulose sold under the name CELLOSIZE WP 3H by UNION CARBIDE | 2.4 g AS |
| preservatives qs | |
| monoethanolamine qs | pH = 9.5 |
| demineralized water qs | 100.0 g |
| COMPOSITION (B) | |
| 6-aminoindole | 2.2 g |
| ethyl alcohol | 10.0 g |
| sodium lauryl ether-sulphate containing 2 moles of ethylene oxide, sold under the name SACTIPON 8533 by LEVER | 5.0 g AS |
| sodium hydroxide solution qs | pH = 8.5 |

| | |
|---|---|
| demineralized water qs | 100.0 g |

Composition (A) is applied for 5 minutes to grey hair which is 90% white. The hair is rinsed and composition (B) is then applied for 10 minutes. The hair is rinsed and dried. The hair is then dyed in a matt deep golden blonde hue.

EXAMPLE 12

| COMPOSITION (A) | |
|---|---|
| cerium (III) chloride containing 7 moles of water | 1.0 g |
| guar gum derivative sold under the name JAGUAR BP 60 by MEYHALL | 0.42 g |
| preservatives qs | |
| citric acid qs | pH = 4.5 |
| demineralized water qs | 100.0 g |
| COMPOSITION (B) | |
| 6-aminoindole | 1.5 g |
| ethylene glycol monobutyl ether | 10.0 g |
| nonylphenol containing 9 moles of ethylene oxide, sold under the name SINNOPAL NP9 by HENKEL | 15.0 g |
| citric acid qs | pH = 6.0 |
| demineralized water qs | 100.0 g |

Composition (A) is applied for 10 minutes to grey hair which is 90% white. The hair is rinsed and composition (B) is then applied for 10 minutes. After rinsing again and drying, the hair is coloured in a very light matt golden blonde hue.

EXAMPLE 13

| COMPOSITION (A) | |
|---|---|
| copper sulphate containing 5 moles of water | 1.0 g |
| sodium lauryl ether-sulphate containing 2 moles of ethylene oxide, sold under the name SACTIPON 8533 by LEVER | 5.0 g AS |
| hydroxyethylcellulose sold under the name CELLOSIZE WP 3H by UNION CARBIDE | 2.4 g AS |
| preservatives qs | |
| monoethanolamine qs | pH = 9.5 |
| demineralized water qs | 100.0 g |
| COMPOSITION (B) | |
| 5-aminoindole | 0.5 g |
| ethyl alcohol | 10.0 g |
| sodium lauryl ether-sulphate containing 2 moles of ethylene oxide, sold under the name SACTIPON 8533 by LEVER | 5.0 g AS |
| sodium hydroxide solution qs | pH = 8.5 |
| demineralized water qs | 100.0 g |

Grey hair which is 90% white is treated for 5 minutes with composition (A). The hair is rinsed and composition (B) is then applied for 10 minutes. The hair is rinsed again and dried. The hair is then dyed in a matt golden blonde hue.

EXAMPLE 14

| COMPOSITION (A) | |
|---|---|
| potassium permanganate | 0.4 g |
| hydrochloric acid qs | pH = 3 |
| demineralized water qs | 100.0 g |
| COMPOSITION (B) | |
| 4-aminoindole | 0.5 g |
| ethylene glycol monobutyl ether | 12.0 g |
| nonylphenol containing 9 moles of ethylene oxide, | 20.0 g |

-continued

| | |
|---|---|
| sold under the name SINNOPAL NP9 by HENKEL | |
| citric acid qs | pH = 5 |
| demineralized water qs | 100.0 g |

Composition (A) is applied for 15 minutes to grey hair which is 90% white. The hair is rinsed and composition (B) is then applied for 20 minutes. The hair is rinsed and dried. The hair is then coloured in a deep ashy blonde hue.

EXAMPLE 15

| COMPOSITION (A) | |
|---|---|
| 2,3-dimethyl-5-amino-6-hydroxyindole dihydrobromide | 1.0 g |
| ethylene glycol monobutyl ether | 12.0 g |
| nonylphenyl containing 9 moles of ethylene oxide, sold under the name SINNOPAL NP9 by HENKEL | 20.0 g |
| triethanolamine qs | pH = 3.7 |
| demineralized water qs | 100.0 g |
| COMPOSITION (B) | |
| sodium metaperiodate | 3.5 g |
| ethyl alcohol | 5.0 g |
| citic acid qs | pH = 4 |
| demineralized water qs | 100.0 g |

Composition (A) is applied for 20 minutes to grey hair which is 90% white. After rinsing, composition (B) is applied for 15 minutes. The hair is rinsed again and dried. A golden blonde is finally obtained.

EXAMPLE 16

| | |
|---|---|
| 6-N-$\beta$-hydroxyethylaminoindole | 1.0 g |
| potassium iodide | 1.0 g |
| ethyl alcohol | 10.0 g |
| guar gum derivative sold under the name JAGUAR HP 60 by MEYHALL | 1.0 g |
| glycoside alkyl ether sold under the name TRITON CG 110 by ROHM & HAAS | 5.0 g AS |
| preservatives qs | |
| spontaneous | pH = 7.2 |
| demineralized water qs | 100.0 g |

This composition is applied for 15 minutes to grey hair which is 90% white. The hair is rinsed and an oxidizing mil at pH 3 assaying at 12.5 volume hydrogen peroxide is then applied for 5 minutes. Finally, the hair is dyed in a deep blonde hue with a very matt ashy glint.

EXAMPLE 17

| COMPOSITION (A) | |
|---|---|
| 4-aminoindole | 0.6 g |
| ethyl alcohol | 10.0 g |
| guar gum derivative sold under the name JAGUAR HP 60 by MEYHALL | 1.0 g |
| glycoside alkyl ether sold under the name TRITON CG 110 by ROHM & HAAS | 5.0 g AS |
| preservatives qs | |
| spontaneous | pH = 6.9 |
| demineralized water qs | 100.0 g |
| COMPOSITION (B) | |
| sodium metaperiodate | 5.0 g |
| hydrochloric acid qs | pH = 3 |
| demineralized water qs | 100.0 g |

Composition (A) is applied for 15 minutes to grey hair which is 90% white. The hair is rinsed and composition (B) is then applied for 15 minutes. The hair is rinsed again and then dried. Hair coloured in a matt ashy deep blonde hue is obtained.

EXAMPLE 18

| COMPOSITION (A) | |
|---|---|
| 5-aminoindole | 0.5 g |
| ethyl alcohol | 10.0 g |
| guar gum derivative sold under the name JAGUAR HP 60 by MEYHALL | 1.0 g |
| glycoside alkyl ether sold under the name TRITON CG 110 by ROHM & HAAS | 5.0 g AS |
| preservatives qs | |
| spontaneous | pH = 7.5 |
| demineralized water qs | 100.0 g |
| COMPOSITION (B) | |
| sodium metaperiodate | 5.0 g |
| hydrochloric acid qs | pH = 3 |
| demineralized water qs | 100.0 g |

Composition (A) is applied for 15 minutes to grey hair which is 90% white. The hair is rinsed and composition (B) is then applied for 15 minutes. The hair is rinsed again and then dried. Finally, the hair is dyed in a beige golden blonde hue.

EXAMPLE 19

| COMPOSITION (A) | |
|---|---|
| 6-N-$\beta$-hydroxyethylaminoindole | 1.0 g |
| ethylene glycol monoethyl ether | 10.0 g |
| sodium lauryl ether-sulphate containing 2 moles of ethylene oxide, sold under the name SACTIPON 8533 by LEVER | 5.0 g AS |
| citric acid qs | pH = 7 |
| demineralized water qs | 100.0 g |
| COMPOSITION (B) | |
| sodium metaperiodate | 3.5 g |
| ethyl alcohol | 5.0 g |
| citric acid qs | pH = 4 |
| demineralized water qs | 100.0 g |

Composition (A) is applied for 20 minutes to grey hair which is 90% white. After rinsing, composition (B) is applied for 15 minutes. The hair is then rinsed again and dried. The hair is finally coloured in an ashy deep blonde hue.

EXAMPLE 20

| COMPOSITION (A) | |
|---|---|
| 7-aminoindole | 1.0 g |
| ethyl alcohol | 10.0 g |
| guar gum derivative sold under the name JAGUAR HP 60 by MEYHALL | 1.0 g |
| glycoside alkyl ether sold under the name TRITON CG 110 by ROHM & HAAS | 5.0 g AS |
| preservatives qs | |
| spontaneous | pH = 6.7 |
| demineralized water qs | 100.0 g |
| COMPOSITION (B) | |
| sodium metaperiodate | 5.0 g |
| hydrochloric acid qs | pH = 3 |
| demineralized water qs | 100.0 g |

Composition (A) is applied for 20 minutes to grey hair which is 90% white. The hair is rinsed and composition (B) is then applied for 15 minutes. After rinsing and drying, hair coloured in a deep blonde hue is obtained.

EXAMPLES 21 TO 25

Hair is dyed by applying 60 g of the colouring composition below. The composition is allowed to act for 10 minutes. The hair is then rinsed with an abundant amount of water and rubbed dry and 75 g of the oxidizing composition below is then applied, this composition being allowed to remain on the hair for 10 minutes for Examples 21 to 23 and for 20 minutes for Examples 24 to 25. After rinsing and shampooing, the colouring indicated at the bottom of the table is obtained.

| | in g | | | | |
|---|---|---|---|---|---|
| | 21 | 22 | 23 | 24 | 25 |
| Colouring composition | | | | | |
| 6-aminoindole | 2 | | | | |
| 5-aminoindole | | 0.5 | | | |
| 6-β-hydroxy-ethylaminoindole | | | 2 | | |
| 4-aminoindole | | | | 1 | |
| 6-amino-2,3-dimethyl-5-hydroxyindole.2HBr | | | | 0.5 | |
| 5,6-dihydroxyindole | | | | | 0.5 |
| ethyl alcohol | 10 | 10 | 10 | 10 | |
| hydroxyethylcellulose sold under the name NATROSOL 250 HHR by HERCULES | 1 | 1 | 1 | 1 | |
| glycoside alkyl ether sold as 60% AS under the name TRITON CG 110 by SEPPIC | 5 (AS) | 5 (AS) | 5 (AS) | 5 (AS) | |
| sodium lauryl ether-sulphate containing 28% AS | | | | | 4.2 (AS) |
| ethylene glycol monobutyl ether | | | | | 10 |
| triethanolamine qs pH | | | | | 5.2 |
| spontaneous pH | 6.5 | 6.5 | 6.5 | 6.9 | |
| water qsp | 100 | 100 | 100 | 100 | 100 |
| Oxidizing composition: | ⅓A + ⅔B | ⅓A + ⅔B | ⅓A + ⅔B | ⅓A + ⅔B | ⅓A + ⅔B |
| A) | | | | | |
| oxyethylenated nonylphenol containing 4 moles of ethylene oxide | 26 | 26 | 26 | 26 | 26 |
| oxyethylenated nonylphenol containing 9 moles of ethylene oxide | 24 | 24 | 24 | 24 | 24 |
| ethylene glycol monobutyl ether | 13 | 13 | 13 | 13 | 13 |
| propylene glycol | 8 | 8 | 8 | 8 | 8 |
| 20% aqueous ammonia solution | 19 | 19 | 19 | | 19 |
| monoethanolamine | | | | 8 | |
| oleic acid diethanolamide | 3.5 | 3.5 | 3.5 | 3.5 | 3.5 |
| perfumes, preservatives, sequestering agent | qs | qs | qs | qs | qs |
| water qs | 100 | 100 | 100 | 100 | 100 |
| B) | | | | | |
| 20 volume hydrogen peroxide | | | | | |
| Hues obtained: | golden coppery deep blonde | coppery deep auburn | ashy golden blonde | golden beige blonde | deep matt golden blonde |

EXAMPLE 26

COMPOSITION (A)

| | |
|---|---|
| 2,3-dimethyl-6-aminoindole hydrochloride | 1.0 g |
| potassium iodide | 1.0 g |
| hydroxyethylcellulose sold under the name NATROSOL 250 HHR by AQUALON | 1.0 g |
| glycoside alkyl ether sold as 60% AS under the name TRITON CG 110 by ROHM & HAAS | 5.0 g AS |
| sodium lauryl ether-sulphate | 0.2 g AS |
| triethanolamine qs | pH = 6.5 |
| demineralized water qs | 100.0 g |

COMPOSITION (B)

12.5 volume hydrogen peroxide solution.

Composition (A) is applied for 15 minutes to grey hair which is 90% white. After rinsing, composition (B) is applied for 15 minutes. The hair is rinsed, washed with shampoo and dried.

The hair is dyed a light golden ashy blonde.

EXAMPLE 27

The procedure is as in Example 26, using 1 g of 2,3,7-trimethyl-6-aminoindole hydrochloride instead of 2,3-dimethyl-6-aminoindole hydrochloride.

The dyeing is carried out on permanent-waved grey hair. This is coloured coppery pearly blonde.

EXAMPLE 28

COMPOSITION (A)

| | |
|---|---|
| 2,3,5-trimethyl-6-aminoindole hydrochloride | 0.5 g |
| potassium iodide | 0.5 g |
| hydroxyethylcellulose sold under the name NATROSOL 250 HHR by AQUALON | 1.0 g |
| glycoside alkyl ether sold as 60% AS under the name TRITON CC 110 by ROHM & HAAS | 5.0 g AS |
| triethanolamine qs | pH = 6.5 |
| demineralized water qs | 100.0 g |

COMPOSITION (B)

12.5 volume hydrogen peroxide solution.

Composition (A) is applied for 15 minutes to permanent-waved grey hair. After rinsing, composition (B) is applied for 15 minutes. After rinsing and shampooing, the hair is dyed light golden ashy blonde.

EXAMPLE 29

| COMPOSITION (A) | |
|---|---|
| copper sulphate containing 5 molecules of water | 1.0 g |
| sodium lauryl ether-sulphate containing 2 moles of ethylene oxide, sold under the name SACTIPON 8533 by LEVER | 3.0 g AS |
| monoethanolamine qs | pH = 9.5 |
| demineralized water qs | 100.0 g |
| COMPOSITION (B) | |
| 2,3,4,5-tetramethyl-6-aminoindole mono-hydrochloride | 0.25 g |
| sodium lauryl ether-sulphate containing 2 moles of ethylene oxide, sold under the name SACTIPON 8533 by LEVER | 4.2 g AS |
| ethylene glycol monobutyl ether | 10.0 g |
| 2-amino-2-methylpropan-1-ol qs | pH = 8.9 |
| demineralized water qs | 100.0 g |

Composition (A) is applied for 10 minutes to grey hair which is 90% white. After rinsing, the hair is treated for 15 minutes with composition (B). After rinsing again and drying, the hair is coloured a matt very light golden blonde hue.

EXAMPLE 30

| COMPOSITION (A) | |
|---|---|
| sodium metaperiodate | 5.0 g |
| hydrochloric acid qs | pH = 3.0 |
| demineralized water qs | 100.0 g |
| COMPOSITION (B) | |
| 2,3,4,5-tetramethyl-6-aminoindole mono-hydrochloride | 0.25 g |
| sodium lauryl ether-sulphate containing 2 moles of ethylene oxide, sold under the name SACTIPON 8533 by LEVER | 4.2 g AS |
| ethylene glycol monobutyl ether | 10.0 g |
| 2-amino-2-methylpropan-1-ol qs | pH = 8.9 |
| demineralized water qs | 100.0 g |

Composition (A) is applied for 10 minutes to grey hair which is 90% white. The said hair is rinsed and treated for 15 minutes with composition (B). The hair is rinsed against and dried. The hair is then coloured in an pearly coppery blonde hue.

EXAMPLE 31

| COMPOSITION (A) | |
|---|---|
| potassium permanganate | 1.2 g |
| hydrochloric acid qs | pH = 5.0 |
| demineralized water qs | 100.0 g |
| COMPOSITION (B) | |
| 2-methyl-6-aminoindole | 0.1 g |
| N-methyl-6-hydroxyethylaminoindole monohydrochloride | 0.1 g |
| 2,3-dimethyl-5-chloro-6-aminoindole monohydrochloride | 0.05 g |
| nonylphenol containing 9 moles of ethylene oxide, sold under the name SINNOPAL NP 9 by HENKEL | 3.0 g |
| polyethylene glycol 300 | 10.0 g |
| tetradecyltrimethylammonium bromide | 0.1 g |
| ethylene glycol monoethyl ether | 4.0 g |
| triethanolamine qs | pH = 6.6 |
| demineralized water qs | 100.0 g |

Composition (A) is applied for 10 minutes to grey hair which is 90% white and the hair is rinsed. Composition (B) is then applied for 15 minutes and the hair is rinsed again. Then air then has a golden coppery light chestnut colouring.

EXAMPLE 32

| COMPOSITION (A) | |
|---|---|
| copper sulphate containing 5 molecules of water | 1.0 g |
| sodium lauryl ether-sulphate containing 2 moles of ethylene oxide, sold under the name SACTIPON 8533 by LEVER | 3.0 g AS |
| monoethanolamine qs | pH = 9.5 |
| demineralized water qs | 100.0 g |
| COMPOSITION (B) | |
| 2,3-dimethyl-5-ethyl-6-aminoindole monohydrochloride | 0.2 g |
| amphoteric surfactant termed cocoamphocarboxyglycinate in the CFTA dictionary, sold under the name MIRANOL C2M by MIRANOL | 3.0 g AS |
| propane-1,2-diol | 12.0 g |
| sodium hydroxide solution qs | pH = 7.8 |
| demineralized water qs | 100.0 g |

Grey hair which is 90% white is impregnated for 10 minutes with composition (A). After rinsing, it is impregnated for 15 minutes with composition (B). After final rinsing and drying, hair dyed a golden beige blonde hue is obtained.

EXAMPLE 23

| COMPOSITION (A) | |
|---|---|
| 2-methyl-5-hydroxy-6-aminoindole dihydrobromide | 0.25 g |
| 2,3-dimethyl-5-hydroxy-6-aminoindole dihydrobromide | 0.15 g |
| amphoteric surfactant termed cocoamphocarboxyglycinate in the CTFA dictionary, sold under the name MIRANOL C2M by MIRANOL | 4.0 g |
| ethylene glycol monobutyl ether | 8.0 g |
| ethanol | 3.0 g |
| N,N-dimethylaminoethanol qs | pH = 7.6 |
| demineralized water qs | 100.0 g |
| COMPOSITION (B) | |
| sodium nitrite | 1.0 g |
| hydrochloric acid qs | pH = 3.0 |
| demineralized water qs | 100.0 g |

Grey hair which is 90% white is treated for 15 minutes with composition (A). After rinsing, said hair is treated for 10 minutes with composition (B). The hair is rinsed again and dried. The hair is finally coloured a copper golden deep blonde hue.

EXAMPLE 34

| COMPOSITION (A) | |
|---|---|
| 2-methyl-6-aminoindole | 0.6 g |
| sodium lauryl ether-sulphate containing 2 moles of ethylene oxide, sold under the name SACTIPON 8533 by LEVER | 2.8 g AS |
| nonylphenol containing 9 moles of ethylene oxide, sold under the name SINNOPAL NP 9 by HENKEL | 3.0 g |
| propylene glycol monomethyl ether | 12.0 g |
| demineralized water qs | 100.0 g |
| spontaneous | pH = 8.5 |
| COMPOSITION (B) | |
| sodium metaperiodate | 5.0 g |
| hydrochloric acid qs | pH = 3.6 |
| demineralized water qs | 100.0 g |

Composition (A) is applied for 15 minutes to grey hair which is 90% white. After rinsing, the hair is treated for 10 minutes with composition (B) and then rinsed again. After drying, a coppery golden blonde colouring is obtained on this hair.

EXAMPLE 35

Composition (A) and (B) are identical to those in Example 34.

The sequence of application of the two compositions is merely reversed, maintaining their respective exposure times.

Hair dyed a coppery deep blonde hue is finally obtained.

EXAMPLE 36

| | |
|---|---|
| 2-methyl-6-aminoindole | 1.0 g |
| potassium iodide | 1.0 g |
| ethylene glycol monobutyl ether | 10.0 g |
| hydroxyethylcellulose is sold under the name NATROSOL 250 HHR by AQUALON | 1.0 g |
| glycoside alkyl ether is sold under the name TRITON CG 110 by ROHM & HAAS | 5.0 g AS |
| preservatives qs | |
| demineralized water qs | 100.0 g |

| -continued | |
|---|---|
| spontaneous | pH = 7.4 |

This Composition is applied for 15 minutes to grey hair which is 90% white. The hair is rinsed and then an oxidizing milk at pH 3 assaying at 12.5 volume hydrogen peroxide is applied for 5 minutes. After rinsing again, the hair is shampooed and dried. The hair is finally coloured a deep golden copper blonde hue.

EXAMPLE 37

In the composition of Example 36, 2-methyl-6-aminoindole is replaced by the same amount of 6-N-($\beta$,$\gamma$-dihydroxypropyl)aminoindole. The dyeing conditions are identical.

The hair is coloured a deep blonde hue.

What is claimed is:

1. A method for dyeing keratinous fibers comprising applying to said fibers a composition (A) containing in a medium suitable for dyeing said fibers at least one aminoindole having the formula

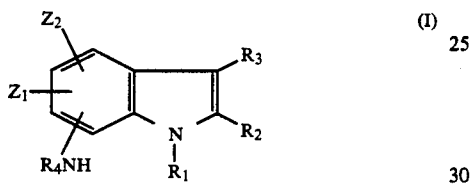

wherein $R_1$ and $R_3$, each independently, represent hydrogen or $C_1$-$C_4$ alkyl, $R_2$ represents hydrogen, $C_1$-$C_4$ alkyl or COOR' wherein R' is hydrogen or $C_1$-$C_4$ alkyl, $R_4$ represents hydrogen, $C_1$-$C_4$ alkyl, $C_1$-$C_4$ hydroalkyl or $C_2$-$C_4$ polyhydroxyalkyl $Z_1$ represents hydrogen, halogen, $C_1$-$C_4$ alkyl or OR wherein R represents hydrogen or $C_1$-$C_4$ alkyl, and $Z_2$ represents hydrogen or $C_1$-$C_4$ alkyl, or a salt thereof, said aminoindole of formula (I) being present in an amount ranging from 0.01 to 5 percent by weight based on the total weight of said composition and developing the color on the said fibers using an oxidizing system selected from (i) iodide ions and hydrogen peroxide, in which case said composition (A) also contains either (a) iodide ions present in an amount ranging from 0.007 to 4 percent by weight, expressed as I$^-$ ions, relative to the total weight of said composition (A), or (b) hydrogen peroxide at a pH ranging from 2 to 7, the application of said composition (A) being preceded or followed by the application of a composition (B) containing in a medium suitable for dyeing said fibers either (a') hydrogen peroxide at a pH ranging from 2 to 12 when said composition (A) contains iodide ions, or (b') iodide ions at a pH ranging from 3 to 11 when said composition (A) contains hydrogen peroxide;

(ii) a nitrate, in which case the application of said composition (A) is followed by the application to said fibers of an aqueous composition (B) having an acid pH, said composition (A) or said composition (B) containing at least one nitrite present in an amount ranging from 0.02 to 1 mole/liter;

(iii) an oxidizing agent selected from the group consisting of periodic acid or a water soluble salt thereof, sodium hypochlorite, potassium ferricyanide, silver oxide, Fenton's reagent, lead (IV) oxide, cesium sulfate and ammonium persulfate, said oxidizing agent being present in said composition (A) in an amount ranging from 0.004 to 0.07 mole per 100 g of said composition (A), or separately applying said oxidizing agent to said fibers at the same time or subsequently, by means of a composition (B) containing said oxidizing agent in a medium suitable for dyeing said fibers;

(iv) metal anions selected from the group consisting of permanganates and bichromates, present in a molar amount of more than $10^{-3}$ mole/1000 g of an aqueous composition (B) having a pH ranging from 2 to 10, said composition (B) being applied to said fibers prior to the application of said composition (A) thereto;

(v) a salt of a metal of Groups III to VIII of the periodic table, said salt being applied to said fibers in a separate step by means of a composition (B) containing said salt in a medium suitable for dyeing said fibers, said salt being present in an amount ranging from 0.01 to 2 percent, expressed as metal ion; or (vi) a rare earth salt present in a composition (B) comprising a medium suitable for dyeing said fibers, said rate earth salt being present in an amount ranging from 0.1 to 8 percent by weight relative to the total weight of said composition (B), said composition (B) being applied to said fibers prior to or subsequent to the application of said composition (A) to said fibers.

2. The method of claim 1 wherein said aminoindole of formula (I) is selected from the group consisting of 4-aminoindole,
5-aminoindole,
6-aminoindole,
7-aminoindole,
5-amino-6-methoxy-2,3-dimethylindole,
6-amino-5-methoxy-2,3-dimethylindole,
5-amino-6-hydroxy-2,3-dimethylindole,
5-hydroxy-6-amino-2,3-dimethylindole,
6-N-$\beta$-hydroxyethylaminoindole,
6-N-$\beta$-hydroxyethylamino-1-methylindole,
6-methylaminoindole,
(5 or 6) amino-N-methylindole,
2-carboxy-6-aminoindole,
4-amino-2,3-dimethylindole,
6-amino-2,3-dimethylindole,
7-amino-2,3-dimethylindole,
6-amino-3-ethyl-2-methylindole,
6-amino-3-methylindole,
6-amino-2-methylindole,
6-amino-2-ethoxycarbonylindole,
7-amino-3-ethyl-2-methlyindole,
6-N-($\beta$,$\delta$-dihydroxypropyl)aminoindole,
2,3,4,5-tetramethyl-6-aminoindole,
2,3-dimethyl-5-chloro-6-aminoindole,
2,3-dimethyl-5-ethyl-6-aminoindole,
2,3,4-trimethyl-6-aminoindole,
2-methyl-5-hydroxy-6-aminoindole,
4-methylaminoindole, 4-amino-1-methylindole,
2,3-dimethyl-6-aminoindole,
2,3,7-trimethyl-6-aminoindole,
2,3,5-trimethyl-6-aminoindole and
a salt thereof.

3. A method for dyeing keratinous fibers comprising applying to said fibers a tinctorial composition containing, in a cosmetically acceptable carrier having a pH less than or equal to 7, at least one indole derivative having the formula

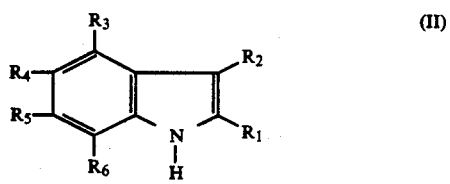

wherein
$R_1$ and $R_2$, each independently, represent hydrogen or $CH_3$,
$R_3$ represents H, $NH_2$, OH or $-OCH_3$,
$R_4$ represents H, $NH_2$, OH or $-OC_2H_5$,
$R_5$ represents H, $NH_2$, OH or $-NHCH_2CH_2OH$, and
$R_6$ represents H or OH,
at least two of the radicals $R_3$, $R_4$, $R_5$ and $R_6$ represent hydrogen, and at least one and only one of the groups $R_3$, $R_4$ or $R_5$ represents $NH_2$, or $-NHCH_2CH_2OH$ for $R_5$; and when $R_5$ represents an amino group and $R_4$ represent OH, $R_1$ and $R_2$ represents a methyl group, and the salts of corresponding acids, said aminoindole of formula (II) being present in an amount ranging from 0.01 to 5 percent by weight based on the total weight of said composition,
permitting said composition to remain in contact with said fibers for a sufficient exposure time,
finishing and drying said fibers,
applying to said rinsed and dried fibers an alkaline oxidizing solution and thereafter
rinsing and shampooing said fibers.

4. The method of claim 3 wherein said aminoindole of formula (II) is selected from the group consisting of
4-aminoindole,
5-aminoindole,
6-aminoindole,
6-amino-2,3-dimethyl-5-hydroxyindole and
6-β-hydroxyethylaminoindole.

5. The method of claim 1 wherein said composition (A), containing in a medium suitable for dyeing said fibers, the aminoindole of formula (I) in combination with iodide ions, is applied to said fibers, the application of said composition (A) being preceded or followed by the application of a composition (B) which contains hydrogen peroxide in a medium suitable for dyeing said fibers.

6. The method of claim 1 wherein said iodide ions are selected from alkali metal iodides, alkaline earth metal iodides or ammonium iodide.

7. The method of claim 1 wherein said iodide ions are present in an amount ranging from 0.08 to 1.5 percent by weight, expressed as $I^-$ ions, relative to the total weight of said composition (A) or said composition (B).

8. The method of claim 1 wherein said nitrite is selected from alkali metal nitrite, alkaline earth metal nitrate, ammonium nitrite, or an organic derivative of a nitrite or nitrite carrier.

9. The method of claim 1 wherein said salt of a metal of Groups III to VIII of the periodic table is selected from a manganeses, cobalt, iron, copper or silver salt.

10. The method of claim 9 wherein said subsequent to the application of compositions (A) and (B) to said fibers, said fibers are rinsed and then contacted with a hydrogen peroxide solution to lighten the color obtained.

11. The method of claim 1 wherein said rare earth salt is selected from the curium $Ce^{3+}$ salt, a cerium $Ce^{4+}$ salt, a lanthanum $La^{3+}$ salt, a europium $Eu^{2+}$ salt, a europium $Eu^{3+}$ salt, a gadolinium $Gd^{3+}$ salt, a ytterbium $Yb^{2+}$ salt, a ytterbium $Yb^{3+}$ salt or a dysprosium $Dy^{3+}$ salt.

12. The method of claim 1 wherein said hydrogen peroxide solution is a 2 to 10 volume hydrogen peroxide solution.

13. The method of claim 1 wherein said composition (A) contains said aminoindole of formula (I) in an amount ranging from 0.03 to 2.5 percent by weight based on the total weight of said composition (A).

14. The method of claim 3 wherein said indole derivative of formula (II) is present in said tinctorial composition in an amount ranging from 0.03 to 2.5 percent by weight based on the total weight of said composityin.

15. The method of claim 1 wherein said compositions (A) and (B) are in the form of a lotion, a cream, a foam, a gel or packaged in an aerosol.

16. The method of claim 1 wherein said medium suitable for dyeing said fibers is a cosmetically acceptable aqueous medium comprising water or a water/solvent mixture.

17. The method of claim 16 wherein said solvent is selected from ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, ethylene glycol monoethyl ether acetate, propylene glycol monomethyl ether, dipropylene glycol monomethyl ether and methyl lactate.

18. The method of claim 1 wherein said medium suitable for dyeing said fibers is an anhydrous solvent medium.

19. The method of claim 18 wherein said solvent is selected from ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, ethylene glycol monoethyl ether acetate, propylene glycol monomethyl ether, dipropylene glycol monomethyl ether and methyl lactate.

20. The method of claim 1 wherein said composition (A) has a pH ranging from 2 to 7.

21. The method of claim 1 wherein said composition (A) has a pH ranging from 3.5 to 7.

22. The method of claim 1 wherein said composition (A) or said composition (B) or both contain at least one of a fatty amide, a surfactant, a thickener, a perfume, a sequestering agent, a film-forming agent, at treatment agent, a dispersing agent, a conditioning agent, a preservative, an opacifying agent and an agent for swelling keratinous fibers.

23. The method of claim 1 wherein said composition also contains an indole dye other than the aminoindole of formula (I).

24. The method of claim 23 wherein the indole dye other than the aminoindole of formula (I) is selected from 5,6-dihydroxyindole, 5,6-dihydroxy-2-carboxyindole, 2-methyl-5,6-dihydroxyindole or a corresponding acid addition salt thereof.

25. The method of claim 3 wherein said oxidizing solution contains an oxidizing agent selected from hydrogen peroxide, urea peroxide, alkali metal percarbonate, alkali metal perborate, ammonium percarbonate and ammonium perborate.

26. The method of claim 3 wherein the alkaline agent employed in said oxidizing solution is ammonia or an alkanolamine.

27. The method of claim 25 wherein the amount of said oxidizing agent in said oxidizing solution ranges from 1 to 10 percent by weight relative to the total weight of oxidizing solution.

28. The method of claim 25 wherein the amount of said oxidizing agent in an oxidizing solution ranges from 1 to 5 percent by weight.

29. An agent for dyeing keratinous fibers comprising composition (A) and composition (B) each defined in claim 1.

30. A multi-compartment device for dyeing keratinous fibers comprising a first compartment containing in a medium suitable for dyeing keratinous fibers composition (A) comprising the aminoindole of formula (I) as defined in claim 1, and a second compartment containing in a medium suitable for dyeing keratinous fibers composition (B) also defined in claim 1.

31. A composition for use in dyeing keratinous fibers comprising in a medium suitable for dyeing said keratinous fibers at least one aminoindole of formula I as defined in claim 1 and present in an amount ranging from 0.01 to 5 percent by weight based on the total weight of said composition and iodide ions present in an amount ranging from 0.007 to 4 percent by weight, expressed as I⁻ ions, relative to the total weight of said composition.

32. A composition for use in dyeing keratinous fibers comprising in a medium suitable for dyeing said keratinous fibers at least one aminoindole of formula I as defined in claim 1 and present in an amount ranging from 0.01 to 5 percent by weight based on the total weight of said composition and at least one nitrite present in an amount ranging from 0.02 to 1 mole/liter of said composition.

33. A method for dyeing keratinous fibres comprising applying to said fibers a composition (A) containing in a medium suitable for dyeing said fibers at least one aminoindole having the formula

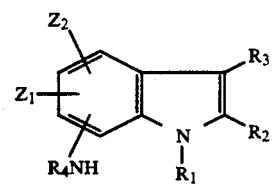

wherein
$R_1$ and $R_3$, each independently, represent hydrogen or $C_1$–$C_4$ alkyl, $R_2$ represents hydrogen, $C_1$–$C_4$ alkyl or COOR' wherein R' is hydrogen or $C_1$–$C_4$ alkyl,
$R_4$ represents hydrogen, $C_1$–$C_4$ alkyl, $C_1$–$C_4$ hydroalkyl or $C_2$–$C_4$ polyhydroxyalkyl,
$Z_1$ represents hydrogen, halogen, $C_1$–$C_4$ alkyl or OR wherein R represents hydrogen or $C_1$–$C_4$ alkyl, and
$Z_2$ represents hydrogen or $C_1$–$C_4$ alkyl,
or a salt thereof,
said aminoindole of formula (I) being present in an amount ranging from 0.01 to 5 percent by weight based on the total weight of said composition and developing the color on the said fibers using an oxidizing system selected from
(i) iodide ions and hydrogen peroxide, in which case said composition (A) also contains either
 (a) iodide ions present in an amount ranging from 0.007 to 4 percent by weight, expressed as I⁻ ions, relative to the total weight of said composition (A), or
 (b) hydrogen peroxide at a pH ranging from 2 to 7, the application of said composition (A) being preceded or followed by the application of a composition (B) containing in a medium suitable for dyeing said fibers either
 (a') hydrogen peroxide at a pH ranging from 2 to 12 when said composition (A) contains iodide ions, or
 (b') iodide ions at a pH ranging from 3 to 11 when said composition (A) contains hydrogen peroxide;
(ii) periodic acid or a water soluble salt thereof present in said composition (A) in an amount ranging from 0.004 to 0.07 mole per 100 g of said composition (A), or
separately applying said periodic acid or water soluble salt therefore to said fibers at the same time or subsequently by means of a composition (B) containing said periodic acid or a water soluble salt thereof in a medium suitable for dyeing said fibers;
(iii) permanganate present in a molar amount of more than $10^{-3}$ mole/1000 g of an aqueous composition (B) having a pH ranging from 2 to 10, said composition (B) being applied to said fibers prior to the application of said composition (A) thereto.

34. The method of claim 33 wherein said aminoindole of formula (I) is either 5-aminoindole or 6-aminoindole.

* * * * *